United States Patent

Trager et al.

Patent Number: 5,288,735
Date of Patent: Feb. 22, 1994

[54] TREATMENT OF GLAUCOMA

[76] Inventors: Seymour F. Trager, 14 Sherwood Dr., Plainview, N.Y. 11803; G. Michael Blackburn, 23 Crimicar La., Sheffield, S10 4FA, United Kingdom

[21] Appl. No.: 899,176

[22] Filed: Jun. 15, 1992

Related U.S. Application Data

[63] Continuation of Ser. No. 666,489, Mar. 6, 1991, abandoned, which is a continuation of Ser. No. 432,994, Nov. 8, 1989, abandoned, which is a continuation-in-part of Ser. No. 346,493, May 2, 1989, Pat. No. 4,975,446.

[51] Int. Cl.$^5$ .................. C07D 285/135; A61K 31/41
[52] U.S. Cl. ..................................... 514/363; 548/139
[58] Field of Search ........................ 548/139; 514/363

[56] References Cited

U.S. PATENT DOCUMENTS 5,010,204  4/1991  Antonaroli et al. ............... 548/128

*Primary Examiner*—Robert Gerstl
*Attorney, Agent, or Firm*—Wegner, Cantor, Mueller & Player

[57] ABSTRACT

Method of treating glaucoma in a mammal, comprising administering to the mammal an effective amount of an active water-soluble carbonic anhydrase inhibitor having the formula:

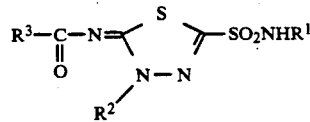

or a pharmaceutically acceptable salt thereof, wherein $R^1$ is selected from the group consisting of H, —OH, —CN and —OCH$_3$, $R^2$ is methyl or a lower alkyl having from two to about 5 carbon atoms, $R^3$ is selected from the group consisting of NHCHR$^4$—, R$^5$NHCHR$^4$—, R$^5$NHCHR$^4$—,

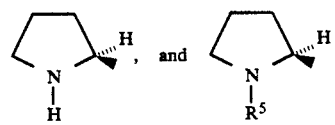

$R^4$ is selected from lower alkyl having from one to about five carbon atoms, or a naturally occurring amino acid side-chain, and $R^5$ is selected from the group consisting of H, CH$_3$—, HCO—, CH$_3$CO— and X—CH$_2$CO— wherein X is a halogen atom and stereoisomers thereof.

33 Claims, No Drawings

TREATMENT OF GLAUCOMA

This application is a continuation of U.S. application Ser. No. 07/666,489 filed Mar. 6, 1991, which is a continuation of U.S. application Ser. No. 07/432,994 filed Nov. 8, 1989, abandoned, which is a continuation-in-part of Ser. No. 346,493 filed May 2, 1989, now U.S. Pat. No. 4,975,446.

BACKGROUND OF THE INVENTION

Approximately one in eight of the persons in the United States registered as blind is handicapped as a direct result of glaucoma. This particular eye affliction may be defined as a rise in intra-ocular pressure which eventually damages the ocular function, with characteristic detrimental changes in the optic nerve and in the visual field, and deterioration of the visual field and sight resulting due to destruction of the optic nerve fibers.

In the normal or healthy eye, the average intra-ocular pressure is about 15.5 mm Hg with an upper limit of about 20.5 mm Hg. A measured intra-ocular pressure on the order of about 22-24 mm Hg is highly suggestive of glaucoma and serves to dictate the desirability of further investigations. Pressures in excess of about 30 mm Hg are most assuredly pathological in nature.

Damage to the eye can begin at intra-ocular pressures of greater than about 21 mm Hg. Additionally, damage to vision can also occur if pressures are below 20 mm Hg with progressive cupping and atrophy of the optic nerve and loss of the visual field, as characteristic in open angle glauooma. In addition to pressures in excess of 30 mm Hg., pressure differentials of greater than about 5 mm Hg. in the eyes of an individual are nearly always suspect of pathological origin.

Glaucoma can be considered as primary and secondary, primary glaucoma being either congenital or capable of developing later in life. The adult onset form of glaucoma can be caused by angle closure, angle obstruction, or resistance to outflow, known as chronic simple glaucoma. Acute angle closure glaucoma results in red, painful eyes, an overt indication that some ocular abnormality exists. In the glaucomic condition termed as chronic simple glaucoma, however, the eyes appear as normal, and such condition can go undiagnosed for a long period of time. This condition can affect newborns, children, the middle-aged and elderly, with a tendency to affect both eyes and produce visual impairment in the latter stages rather than at onset.

The cause of chronic simple glaucoma is as yet largely unknown. In the normal eye, part of the epithelial lining of the inside of the eye, known as the ciliary body or the ciliary epithelium, secretes a fluid known as aqueous humor which circulates within the eye, supplying nutrients and removing waste products. This aqueous humor drains away through a filtering system called the trabecular meshwork into the canal of Schlemm and then into the aqueous veins, with the rate of aqueous production normally about 2 mm$^3$ per minute. It is unlikely that a simple inorease in the rate of aqueous humor output would result in glaucoma without some outflow resistance, and a permanent rise in the intra-ocular pressure is always the result of decreased outflow.

In addition to supplying nutrients and removing waste products, the aqueous humor also provides a constant pressure within the eye, with the normal pressure being from about 15 to about 20.5 mm Hg. In glaucoma this intraocular pressure may rise to as high as 30 mm Hg. and, in some exceptional cases, to about 70 mm Hg., with the damage produced by the increased pressure related to the degree of increase above normal. While some eyes appear to be more resistant to elevated pressures than others, prolonged elevated pressures will produce mechanical and vascular changes and pathology in the eye.

In glaucoma, the actual locus of damage is the optic nerve head, resulting in damage to the retinal nerve fibers passing out of the eye, the nerve fibers responsible for conducting visual impulses from the retina to the brain and damage to which results in visual loss or impairment. The responsibility for the perception of the field of vision resides with retinal receptors and damage thereto necessarily reduces the ability of the affected individual to see part or all of the visual field.

A constant relationship exists between retinal cells and nerve fibers, and as the nerve fiber damage appears in a selective and repeating fashion, the visual field effects may be said to be typical, although not exclusively so, of glaucoma.

The reasons why intra-ocular pressure rises above normal levels are not completely understood, as has been previously stated. In the instance of chronic simple glaucoma, the trabecular meshwork becomes resistant to the outflow of aqueous humor. This condition is known as open angle glaucoma. If the anterior chamber (the angle) becomes blocked by iris tissue the result is a sudden blockage of outflow of the aqueous humor and a concomitant, sudden rise in the pressure levels (closed angle glaucoma). Blockage of the anterior chamber angle can be brought about by any stimulus which enlarges the pupil of the eye, as for example darkness, reading or extended viewing, anxiety, reactions to medications such as adrenalin, and the like.

When the iris is withdrawn from the angle, but synechiae remain in the angle, the aqueous humor is unable to drain away and the intra-ocular pressure remains elevated (chronic congestive glaucoma).

In closed angle glaucoma, provided that the pressure is relatively easy to control, surgical procedures are prescribed, that of peripheral iridectomy wherein a small opening is cut in the iris using standard surgical or laser techniques. This procedure allows the aqueous humor trapped behind the iris to pass into the anterior chamber, which deepens, allowing unobstructed drainage through the angle. Angle closure glaucoma remains primarily a problem best dealt with by the employment of surgical procedures, although medical therapy is required in the initial stages and further may be required following surgery.

Surgery for open angle glaucoma, however, involves bypassing the trabecular meshwork and is dictated for those whose intra-ocular pressure cannot be adequately controlled by medication and for those who cannot or will not use their medication. In this surgical procedure, a small portion of the trabeculum is removed from under the scleral flap.

In spite of the success generally with the operation, management of open angle glaucoma by chemical means remains the first choice of action. The aim in medical as opposed to surgical therapy in glaucoma is to establish and maintain throughout each succeeding twenty-four hour period an intra-ocular pressure sufficiently low to prevent damage occurring within the eye and, in particular, to the optic disc. Since the cause of open angle glaucoma is not known, it is not presently possible to cure the underlying disease, but only to continuously control it.

According to statistics amassed by the National Institute of Health, more than one million individuals in the U.S. alone are afflicted with glaucoma, with females outnumbering males. Every year, on the order of two million visits are made to clinics in the U.S. for the diagnosis and treatment of glaucoma. Although surgical procedures are indicated in many cases, the majority of persons afflicted with glaucoma are subjected to medical, rather than surgical, treatment.

The chemicals which have been used to control glaucoma may be conveniently placed into three categories, dependent upon the primary mode of action: (a) those chemicals which increase the outflow of aqueous humor without affecting the aqueous humor production, (b) those chemicals which decrease the rate of aqueous humor production without affecting the outflow, and (c) those chemicals which affect both production and outflow of the aqueous humor.

The first group (a) encompasses the miotic drugs and the outflow resistance reducers, with the miotics divided into parasympathomimetics and anticholinesterase agents. Parasympathomimetics, the most widely used of which is pilocarpine, stimulate the action of acetylcholine which is responsible for, inter alia, the contraction of the pupil. If parasympathomimetics are administered alone, they are rapidly destroyed by the enzyme cholinesterase present in the blood, the ciliary bodies and the iris.

Anticholinesterase agents block cholinesterase and thereby increase the effect of acetylcholine in the eye. Also, this medication is unstable, readily oxidizing to an inactive form and has many undesirable side effects including conjunctival irritation and allergic reactions. The most potent anticholine agent known is phospholine iodide, a synthetic acetylcholine analogue which binds very strongly to cholinesterase, and which may be used in relatively small amounts. However, the use thereof produces many systemic and ocular side effects, including an increase in the incidence of cataract formation.

There are many disadvantages in the use of miotic drugs in the treatment of glaucoma. Some of the drugs have relatively short durations of activity and therefore require frequent installation, a particular problem among elderly patients among whom the disease is most common. Further, many patients report a darkening of vision due to pupil contraction and a significant diminution of color values. Additional disadvantages include topical allergic manifestations and the formation of iris cysts, as well as transitory discomfort such as nausea, vomiting, diarrhea, excessive salivation, sweating and dizziness.

Recently, a measure of interest has been expressed in the use of Cytochalasin B and ethylene-diaminetetraacetic acid (EDTA) to reduce the aqueous humor outflow resistance.

In the trabecular meshwork and the canal of Schlemm are located cytoplasmic actin microfilaments. Cytochalasin B is known to cause disruption of these filaments. It has been demonstrated that, following injection into the anterior chamber of the eye, Cytochalasin B causes a marked increase in aqueous humor outflow. However, this compound is also very cytotoxic. It is further known that the presence of calcium ions is necessary for cell adhesion and that the removal of calcium ions from the anterior chamber by the administration of EDTA exhibits an effect similar to that of Cytochalasin B. In common with most calcium antagonists, and unfortunately, EDTA is also very toxic.

A second group of drugs, the adrenergic agonists, affect both aqueous humor formation and outflow. The sympathetic effector cells in the eye have both alpha and beta type receptor sites. Stimulation of either of these sites reduces intra-ocular pressure, alpha site stimulation increasing outflow through the trabecular meshwork and beta site stimulation decreasing aqueous humor production at the ciliary body. However, the sympathetic pharmacology of the eye and, conversely, alpha and beta adrenoreceptor blocking agents also produce a lowering of the intra-ocular pressure. Even though adrenergic drugs have been employed in the management of glaucoma for over 60 years, these drugs also exhibit side effects which can be quite marked, the major effects being systemic in nature. Adrenalin and isoprotenerol, both used as adrenergic agents, can produce such side effects as conjunctival hyperaemia and pupil dilation, among others. Adrenalin is further unsuited for use by patients afflicted with cardiovascular diseases or hypertension, particularly significant as glaucoma tends to be a disease of the middle-aged and elderly Guanethidine is a post-ganglionic adrenergic neuron blocker which acts by impairing the release of nonadrenaline from adrenergic nerve junctions. Used alone, this drug has little effect in lowering intraocular pressure and is often used in conjunction with adrenaline, administered prior to adrenaline medication.

Timolol ®, employed as a beta adrenergic blocker, lacks most of the undesirable side effects of pilocarpine, such as miosis, local irritation, headache and ciliary spasm, and also produces less conjunctival hyperemia than adrenalin. However, clinical results which have been obtained on the use of Timolol ® have revealed that, used in eye drops, Timolol ® can cause cardiovascular disturbances including bradycardia and systemic hypotension, some decrease in tear production and occasional bronchiospasms.

The third group of glaucoma treatment drugs are the systemic inhibitors of carbonic anhydrase, reducing intraocular pressure by acting to reduce the formulation of aqueous humor, the most commonly used of which is the 1,3,4-thiadiazole, acetazolamide (Diamox ®). The inhibition of carbonic anhydrase acts to decrease the rate of production of aqueous humor without suppressing the production thereof completely. However, acetazolamide therapy is also associated with metabolic acidosis and, in many patients with renal impairment, this may cause confusion, weakness and pronounced hyperventilation. Further, long term acetazolamide therapy can result in formation of kidney stones, hepatic coma in patients with pre-existent liver diseases and, although rarely so, bone marrow depression. A proposed alternative to the use of acetazolamide has been dichlorphenamide (Daranide). However, the undesirable side effects resulting during the use of this particular therapeutic compound, if anything, are more pronounced than those resulting from the use of acetazolamide.

SUMMARY OF THE INVENTION

This invention relates to certain novel organic compounds having valuable pharmaceutical applications. More particularly, this invention relates to novel sulfonamides exhibiting good water solubilities and excellent inhibitory action on carbonic anhydrase, and to a process for preparation of these compounds. It is a primary objective of the present invention to provide a highly effective, water soluble carbonic anhydrase inhibitor for the treatment of glaucoma.

Another object of the present invention is to provide a medicament which may be used topically in the treatment of glaucoma, which medicament will pass through the five-layered cornea and retain the effectiveness to act therapeutically upon the ciliary body.

A further object of the invention is to provide a highly effective topical medicament for treatment of glaucoma which is non-harmful to the tissues of the eye.

A still further object of the invention is to provide a water soluble prodrug which can be used topically and can be enzymatically hydrolysed by natural agents in the body, specifically aminopeptidases, to give a more hydrophobic inhibitor for carbonic anhydrase with comparable inhibitory activity at the site of application via release of an aminoarylsulfonamide or a 2-amino-1,3,4-thiadiazole-5-sulfonamide or a 2-imino-3-methyl-1,3,4-thiadiazole-5sulfonamide.

The method and manner of achieving the foregoing objectives, as well as others, will become apparent from the detailed description of the invention which follows.

It has been found that compounds of the formula

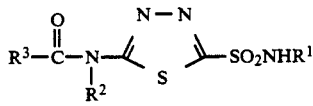

are particularly effective as carbonic anhydrase inhibitors in the treatment of glaucoma. Compounds encompassed by this general formula are those wherein $R^1$ is selected from the group consisting of H, —OH, —CN, and —OCH$_3$;

$R^2$ is hydrogen or a lower alkyl having from one to about 5 carbon atoms;

$R^3$ is selected from the group consisting of HNHCHR$^4$—, R$^5$NHCHR$^4$—, R$^5$NHCHR$^4$CONHCHR$^4$—, R$^5$NHCH$_2$CHR$^4$—,

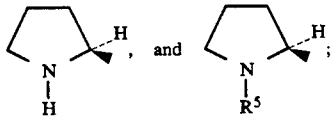

$R^4$ is selected from lower alkyl having from one to about 5 carbon atoms, or a naturally occurring amino acid side chain; and $R_5$ is selected from the group consisting of H, CH$_3$—, HCO—, CH$_3$CO— and XCH$_2$CO— wherein X is a halogen atom; and stereoisomers of all these compounds.

It has been further found that compounds of the formula

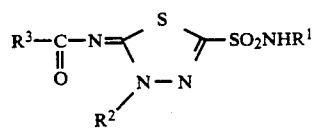

are particularly effective as carbonic anhydrase inhibitors in the treatment of glaucoma. Compounds encompassed by this general formula are those wherein $R^1$ is selected from the group consisting of H, —OH, —CN, and —OCH$_3$;

$R^2$ is a methyl or a lower alkyl having from two to about five carbon atoms;

$R^3$ is selected from the group consisting of HNHCHR$^4$—, RNHCHR$^4$—, R$^5$NHCH$_2$CHR$^4$—,

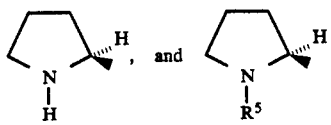

$R^4$ is selected from lower alkyl having from two to five carbon atoms, or a naturally occuring amino acid side chain;

$R^5$ is selected from the group consisting of H, CH$_3$—, HCO—, CH$_3$CO—, and X—CH$_2$CO— wherein X is a halogen atom; and stereoisomers of all of these compounds.

Salts of these compounds have also been found to be useful in the treatment of glaucoma, salts formed from mineral acids such as hydrochloric, hydrobromic, sulfuric, and boric acids; organic mono-, di- and tri-carboxylic acids such as acetic, maleic, tartaric, and citric acids and the like, sulfonic acids such as 4-methylphenylsulfonic acid being particularly efficacious. The preferred salts are those of hydrochloric and citric acids.

Compounds of the present invention are conveniently prepared by chemical synthesis.

In utilizing the compounds in the treatment of glaucoma, the treatment compounds may be administered either systemically or topically in the form of eye drops, tablets, powders or capsules by incorporating the appropriate dosage with carriers according to accepted pharmaceutical practices. Preferably, administration of a selected compound or an acid addition salt thereof is effected by topical application in the form of eye drops.

The novel sulfonamides of the present invention having the formula

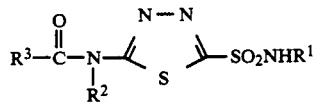

are conveniently prepared by condensing a selected acid reactant with a selected 2-amino-1,3,4-thiadiazole-5-sulfonamide in solution in the presence of a condensation agent. The reaction is depicted in Scheme I:

Scheme I

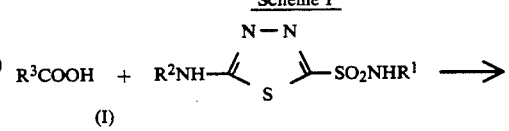

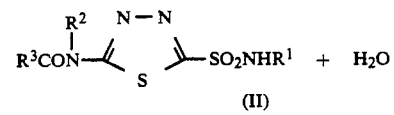

The condensation reaction of (I) and (II) is conveniently effected using a condensing agent, such as isobutyl chloroformate or other alkyl or aryl chloroformates commonly employed in such reactions, in the presence of a base, or using dicyclohexylcarbodiimide with or without a catalyst, or by any other known and appropriate methods for formation of the amide bond, as commonly employed in the synthesis of peptides.

Compounds of the present invention having the formula

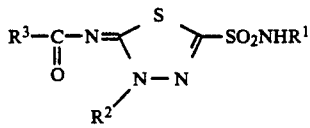

are conveniently prepared by condensing a selected N-protected amino acid reactant with a selected 2-amino-5-benzylthio-1,3,4-thiadiazole in solution in the presence of a condensing agent. The reaction is depicted in Scheme X:

Scheme X

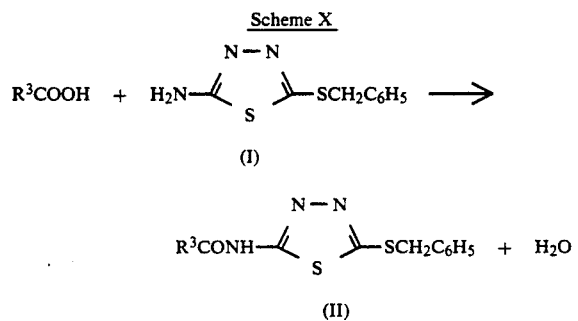

The condensation reaction of (I) and (II) is conveniently effected using a condensing agent such as isobutyl chloroformate, or other alkyl or aryl chloroforms commonly employed in such reactions, in the presence of a base, of using dicylohexylcarbodiimide with or without a catalyst, or by any known and appropriate methods for formation o the amide bond, as commonly employed in the synthesis of peptides.

Such species (II) are then deprotonated by treatment with a base, commonly sodium methoxide or sodium methoxide in alcoholic solution and reacted with an alkylating agent containing from one to five carbon atoms, typically methyl bromide. The resulting 2-N-acylimino-3-alkyl-5-benzylthio-ΔZ-1,3,4-thiadiazoline (III) is treated with chlorine gas in solution in acetic acid and water to convert it into the corresponding thiadiazoline-5-sulphonyl chloride (IV) which is immediately transformed into the thiadiazoline-5-sulphonamide (V) by stirring with liquid ammonia or an appropriate amine. Finally, deprotection of the amino group of the protected amino acid is carried out using a reagent appropriate to the protecting group in question, for example hydrogen bromide in glacial acetic acid for the removal of benzyloxycarbonyl groups.

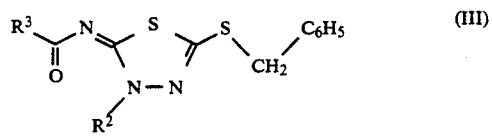

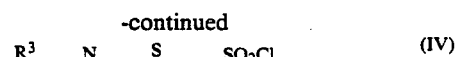

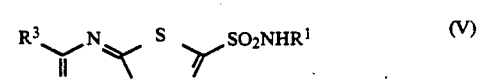

DESCRIPTION OF THE PREFERRED EMBODIMENT

A particularly desirable process for producing the novel sulfonamides of the present invention is one wherein the selected acid reactant, in anhydrous pyridine, is admixed with anhydrous tetrahydrofuran at reduced temperatures, on the order of $-15°$ C., and a condensation agent is added dropwise thereto with stirring, the agent being added in amounts slightly in excess of the molar amount of reactant acid present while maintaining the temperature at reduced values. For preparation of compounds having the formula

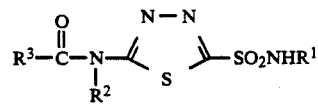

a solution of the selected sulfonamide in anhydrous tetrahydrofuran is then added slowly while maintaining the reaction medium at low temperatures. After a period of stirring under reduced temperatures, on the order of about two hours, the reaction mixture is allowed to warm with stirring, and evaporated to a solid under reduced pressures. The solid is then partitioned in a water: lower alkyl ester wash, and the organic phase separated, washed and dried over a suitable drying agent. The resulting anhydrous solution is then filtered and evaporated under reduced pressure to recover the sulfonamide product as a solid.

The following specific, but not limiting, examples, serve to further illustrate the invention.

EXAMPLE I

Preparation of 2-(N-Carbobenzyloxyglycylamino)-1,3,4-Thiadiazole-5-Sulfonamide

Anhydrous pyridine (3.45 gm, 20 mmole) and 2-(N-carbobenzyloxy)glycine (5.0 gm, 20 mmole) are stirred and admixed in a 250 ml round bottom flask with anhydrous tetrahydrofuran (40 ml) at $-15°$ C. To the stirred flask is added dropwise isobutyl chloroformate (3.0 gm, 22 mmole) and the contents of the flask stirred for an additional 5 minutes. A solution of 2-amino-1,3,4-thiadiazole-5sulfonamide (3.60 gm, 20 mmole) in 150 ml dry tetrahydrofuran is then added slowly at $-15°$ C. while the stirring is continued.

After 2 hours the reaction mixture is allowed to warm to room temperature and the stirring is continued overnight. The mixture is then evaporated to dryness under reduced pressure and the solids partitioned between water and ethyl acetate (1:1, V/V 400 ml). The resulting organic phase is washed with aqueous citric acid (200 ml 10% w/v), 100 ml water, 100 ml saturated brine and dried over anhydrous magnesium sulfate.

After filtration, the solution is evaporated under reduced pressure and crystallized from ethyl acetate:hexane to yield as a product 5.0 gm 2-(N-carbobenzyloxyglycylamino)-1,3,4-thiadiazole-5-sulfonamide as a white solid, having a m.p. 199°-201° C.

EXAMPLE II

Preparation of 2-(N-Carbobenzyloxy-L-Prolylamino)-1,3,4-Thiadiazole-5-Sulfonamide Observing again the reaction and recovery procedures set forth in Example I, replacing the glycyl reactant with 2-(N-carbobenzyloxy)-L-proline, and using 2-amino-1,3,4-thiadiazole-5-sulfonamide, the desired product, 2-(N-carbobenzyloxy-L-prolylamino)-1,3,4-thiadiazole-5-sulfonamide, m.p. 199°-201° C., is obtained.

EXAMPLE III

Preparation of 2-(N-Carbobenzyloxy-L-Alanylamino)-1,3,4-Thiadiazole-5-Sulfonamide Observing again the reaction and recovery procedures set forth in Example I, replacing the L-propyl reactant with 2-(N-carbobenzyloxy)-L-alanine, and using 2-amino-1,3,4-thiadiazole-5-sulfonamide, the desired product, 2-(N-carbobenzyloxy-L-alanylamino)-1,3,4-thiadiazole-5-sulfonamide, m.p. 203°-205° C., [alpha]$_D$−29° (0.4% in ethanol) is obtained.

EXAMPLE IV

Preparation of 2-(N-Carbobenzyloxy-L-Phenylalanylamino)-1,3,4-Thiadiazole-5-Sulfonamide Observing again the reaction and recovery procedures set forth in Example I, replacing the L-propyl reactant with 2-(N-carbobenzyloxy)-L-phenylalanine, and using 2-amino-1,3,4-thiadiazole-5-sulfonamide, the desired product, 2-(N-carbobenzyloxy-L-phenylalanylamino)-1,3,4-thiadiazole-5-sulfonamide, m.p. 192°-194° C., [alpha]$_D$+18° (0.4% in ethanol) is obtained.

EXAMPLE V

Preparation of 2-(Glycylamino)-1,3,4-Thiadiazole-5-Sulfonamide Hydrobromide

The desired compound is prepared by subjecting 2-(N-carbobenzyloxyglycylamino)-1,3,4-thiadiazole-5-sulfonamide (0.5 gram) suspended in glacial acetic acid (5 ml) to a solution of hydrogen bromide in glacial acetic acid (32% w/w, 8.0 ml) at room temperature for 1 hour with stirring. Diethyl ether (50 ml) is then added and the mixture set aside for three hours at 0° C. The solid precipitate is collected, washed with diethyl ether, and dried to give the desired product, 2-(glycylamino)-1,3,4-thiadiazole-5-sulfonamide hydrobromide, m.p. 207°-209° C. (0.4 gram).

EXAMPLE VI

Preparation of 2-(L-Alanylamino)-1,3,4-Thiadiazole-5-Sulfonamide Hydrobromide

Observing again the reaction and recovery procedures set forth in Example V, 2-(N-carbobenzyloxyalanylamino)-1,3,4-thiadiazole-5-sulfonamide prepared as in Example II is converted into the desired product, 2-(L-alanylamino)-1,3,4-thiadiazole-5-sulfonamide hydrobromide, m.p. 193°-197° C.

EXAMPLE VII

Preparation of 2-(L-Phenylalanylamino)-1,3,4-Thiadiazole-5-Sulfonamide Hydrobromide Observing again the reaction and recovery procedures set forth in Example V, 2-(N-carbobenzyloxy-L-phenylalanylamino)-1,3,4-thiadiazole-5-sulfonamide is converted into the desired product, 2-(L-phenylalanylamino)-1,3,4-thiadiazole-5-sulfonamide hydrobromide, m.p. 188°-192° C.

The hydrobromide salts may be converted into the corresponding hydrochloride salts by conventional methods, in particular the use of anion exchange resins, by operations familiar to those skilled in the art. Similar results have been obtained for the hydrochloride salts and for the hydrobromide salts.

For preparation of compounds having the formula

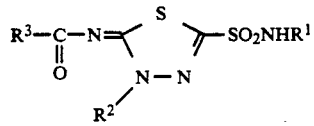

a solution of the 2-amino-5-benzylthio-1,3,4-thiadiazole in anhydrous tetrahydrofuran is then slowly added while maintaining the reaction medium at low temperatures. After a period of stirring under reduced temperature, on the order of about two hours, the reaction mixture is allowed to warm with stirring, and evaporated to a solid under reduced pressures. The solid is then partitioned in a water: lower alkyl ester wash, and the organic phase separated, washed, and dried over a suitable drying agent. The resulting anhydrous solution is then filtered and evaporated under reduced pressure to recover the thiadiazole product as a solid.

The alkylation of this product is accomplished by treating a solution of the 2-N-acylamino-5-benzylthio-1,3,4-thiadiazole in methanol with a solution of sodium methoxide, of the order of one equivalent, followed by an alkylating agent such as ethyl bromide or dimethyl sulphate, of the order of one equivalent. After standing at room temperature overnight, the solution volume is reduced by evaporation under vacuum and diluted with water to precipitate the product. The crude material is slurried with concentrated sodium hydroxide solution to remove unreacted starting thiadiazole and the 2-N-acylamino-3-alkyl-5-benzylthio-1,3,4-thiadiazoline is crystallized for a lower alcohol, preferably methanol.

A solution of this 2-N-acylamino-3-alkyl-5-benzylthio-1,3,4-thiadiazoline product in glacial acetic acid is treated with a small amount of water, of the order of 10% w/w, and cooled to about 15° C. Chlorine gas is then passed into the solution with external cooling to maintain the temperature below about 25° C. After some time, the end of the reaction is signalled by a rapid lowering of the solution temperature and the gas flow is discontinued. The precipitated product is collected by filtration, rapidly washed with ice water, dried, and triturated with ether.

The dry solid is added immediately to a well-stirred volume of liquid ammonia, on the order of 5 parts v/w, and the mixture allowed to evaporate in a stream of air. The resulting solid 2-N-acylamino-3-alkyl-1,3,4-thiadiazoline-5-sulphonamide is purified by crystallization from an appropriate alcohol solvent.

Finally, the above protected 2-N-aminoacyl-3-alkyl-1,3,4-thiadiazoline-5-sulphonamide is deprotected by such process as is appropriate for the specific protecting group on the 2-N-aminoacylamino-function. In the case of the carbobenzyloxy protecting group, this is achieved by dissolution of the above species in glacial acetic acid followed by the addition of a solution of hydrogen bromide in glacial acetic acid and the mixture stirred for about one hour. Diethyl ether is then added and the mixture set aside at 0° C. for about 3 hours. The solid precipitate is collected by filtration, washed with dry diethyl ether, and dried to give the desired 2-N-aminoacyl-3-alkyl-1,3,4-thiadiazoline-5-sulphonamide as its hydrobromide salt.

EXAMPLE VIII

Preparation of
2-(N-Carbobenzyloxyglycylamino)-5-Benzylthio-1,3,4-Thiadiazole

Anhydrous pyridine (3.45 gm, 20 mmole) and N-carbobenzyloxyglycine (5.0 gm, 20 mmole) are stirred and admixed in a round bottom flask with anhydrous tetrahydrofuran (40 ml) at −15° C. To the stirred mixture is added dropwise isobutyl chloroformate (3.0 gm, 22 mmole) and the contents of the flask stirred for an additional 5 minutes. A solution of 2-amino-5-benzylthio-1,3,4-thiadiazole (3.60 gm, 20 mmole) in 150 ml dry tetrahydrofuran is then added slowly at −15° C. while stirring is continued. After 2 hours the reaction mixture is allowed to warm to room temperature and the stirring continued overnight. The mixture is then evaporated to dryness under reduced pressure and the solids partitioned between water and ethyl acetate (1:1, v/v, 400 ml). The resulting organic phase is washed with aqueous citric acid (200 ml 10% w/v), 100 ml water, 100 ml saturated brine, and dried over anhydrous magnesium sulphate.

After filtration, the solution is evaporated under reduced pressure and the product crystallized from ethyl acetate:hexane to yield as a product 5 gm of 2-(N-carbobenzyloxyglycylamino)-5-benzylthio-1,3,4-thiadiazole as a white solid, having a m.p. 200°–202° C.

EXAMPLE IX

Preparation of
2-(L-N-Carbobenzyloxyalanylamino)-5-Benzylthio-1,3,4-Thiadiazole

Observing again the reaction and recovery procedures set forth in Example VIII, replacing the carbobenzyloxyglycine component with 2-L-carbobenzyloxylalanine, the desired product, 2-(L-N-Carbobenzyloxyalanylamino)-3-benzylthio-1,3,4-thiadiazole, m.p. 205°–206° C. is obtained.

EXAMPLE X

Preparation of
2-(L-N-Carbobenzyloxylphenylalanylamino)-5-Benzylthio-1,3,4-Thiadiazole Observing again the reaction and recovery procedures set forth in Example VIII, replacing the carbobenzyloxyglycine with carbobenzyloxy-L-phenylalanine, the desired product, 2-(L-N-carbobenzyloxyphenylalanylamino)-3-benzylthio-1,3,4-thiadiazole m.p. 128°–132° was obtained.

EXAMPLE XI

Preparation of
2-(L-N-Carbobenzyloxyvalylamino)-5-Benzylthio-1,3,4-Thiadiazole

Observing again the reaction and recovery procedures set forth in Example VIII, and replacing the carbobenzyloxyglycine with carbobenzyloxy-L-valine, the desired product 2-(N-Carbobenzyloxyvalylamino)-3-benzylthio-1,3,4-thiadiazole product was obtained, m.p. 215°–220° C.

EXAMPLE XII

Preparation of
2-(N-Carbobenzyloxyglycylimino)-5-Benzylthio-3-Methyl-1,3,4-Thiadiazoline A solution of the product from Example VIII (ca 30 gm, 0.1 mole) in methanol (200 ml)m containing sodium methoxide (from 2.5 g sodium, 0.11 mole) is warmed in a flask fitted with a Dry Ice condenser, stirred 3 hr., then cooled to 5° C. Methyl bromide gas was then passed through the reaction (0.15 mole) and the solution stirred overnight at room temperature. The solution is diluted with water (200 ml) to give a sticky solid, ca25 gm. this is slurried with cold concentrated sodium hydroxide solution to remove starting material Yield 20 gm, 40%, recrystallized from ethanol, 15 gm, m.p. 92° C.

EXAMPLE XIII

Preparation of
2-(N-Carbobenzyloxy-L-Alanylimino)-5-Benzylthio-3-Ethyl-1,3,4-Thiadiazoline Observing again the reaction and recovery procedures set forth in Example XII, and replacing the N-carbobenzyloxyglycylaminothiadiazole reactant with the product of Example IX (0.1 mole) and replacing the methyl bromide of Example XII with ethyl chloride, the desired product, 2(N-Carbobenzyloxy-L-alanylamino)-5-benzylthio-3-ethyl-1,3,4-thiadiazoline, m.p. 101° C., is obtained.

EXAMPLE XIV

Preparation of
2-(N-Carbobenzyloxy-L-Phenylalanylimino)-5-Benzylthio-3-Methyl-1,3,4-Thiadiazoline Observing again the reaction and recovery procedures set forth in Example XII, and replacing the N-carbobenzyloxyglycylaminothiadiazole with 2-(N-Carbobenzyloxy-L-phenylalanylamino)-5-benzylthio-1,3,4-thiadiazole (0.1 mole) from Example III, the desired product, 2-(N-carbobenzyloxy-L-phenylalanylimino)-5-benzylthio-3-methyl-1,3,4-thiadiazoline is obtained, m.p. 131°–134° C.

EXAMPLE XV

Preparation of
2-(N-Carbobenzyloxy-L-Valylimino)-5-Benzylthio-3-Ethyl-1,3,4-Thiadiazoline The product of Example XI (0.1 mole) is dissolved in methanol (200 ml) containing sodium methoxide (from 2.5 gm sodium) and stirred for 3 hr. Dimethyl sulphate (13 gm, 0.1 mole) is added in a single portion and the solution warmed for about 30 minutes. The solution is then cooled and diluted with cold sodium hydroxide solution (200 ml 2 molar). When solidification starts, water (200 ml) is added and the mixture stirred for about 1 hour. The product is collected by filtration, washed with water (500 ml), and dried, m.p. 75°–78° C. The product can be further purified by crystallization from methanol.

EXAMPLE XVI

Preparation of
2-N-Carbobenzyloxyglycylimino-3-Methyl-1,3,4-Thiadiazoline-5-Sulphonamide A solution of the product of Example XII (0.05 mole) in glacial acetic acid (50 gm) is treated with water (5 ml) and cooled to below 15° C. Chlorine gas is bubbled through the mixture until a rapid fall in temperature signals the end of the reaction. The cream-colored precipitate is collected by filtration, washed with ice-water, and pressed dry. After trituration with a minimum volume of cold ether, the product has m.p. 105°. Without further purification, it is added to liquid ammonia in a Dewar vessel (50 ml) and the mixture stirred, then allowed to evaporate in the hood. The solid residue is dissolved in water (75 ml), clarified with animal charcoal, and precipitated by the cautious addition of hydrochloric acid to give the product, m.p. 215°, 80% yield.

EXAMPLE XVII

Preparation of
2-N-Carbobenzyloxy-L-Alanylimino-3-Ethyl-1,3,4-Thiadiazoline-5-Sulphonamide A solution of the product of Example XIII (0.05 mole) in glacial acetic acid (50 gm) is treated with water (5 ml) and cooled below 15° C. and treated with chlorine gas as described in the reaction and recovery procedures of Example XVI. The desired product, 2-N-carbobenzyloxyimino-3-ethyl-1,3,4-thiadiazoline-5-sulphonamide, is obtained as cream-colored crystals, m.p. 206° C., 75% yield.

EXAMPLE XVIII

Preparation of
2-(N-Carbobenzyloxy-L-Phenylalanylimino)-3-Methyl-1,3,4-Thiadiazoline-5-Sulphonamide Observing again the reaction and recovery procedures of Example XVI, a solution of the product of Example XIV (0.05 mole) in glacial acetic acid (50 gm) is converted into the desired product, 2-(N-carboxybenzyloxy-L-phenylalanylimino)-3-methyl-1,3,4-thiadiazoline-5-sulphonamide which is obtained as cream colored crystals, m.p. 224° C., 78% yield.

EXAMPLE XIX

Preparation of
2-(N-Carbobenzyloxy-L-Valylimino)-3-Methyl-1,3,4-Thiadiazoline-5-Sulphonamide Observing again the reaction and recovery procedures of Example XVI, a solution of the product of Example XIV (0.05 mole) in glacial acetic acid (50 gm) is converted into the desired product, 2-(N-carbobenzyloxy-L-valylimino)-3-methyl-1,3,4-thiadiazoline-5-sulphonamide, m.p. 209° C. yield 65%.

EXAMPLE XX

Preparation of
2-(Glycylimino)-3-Methyl-1,3,4-Thiadiazoline-5-Sulphonamide Hydrobromide The desired compound is prepared by subjecting 2-(N-carbobenzyloxy-glycylimino)-3-methyl-1,3,4-thiadiazoline-5-sulphonamide (0.5 gm) suspended in glacial acetic acid (5ml) to a solution of hydrogen bromide in glacial acetic acid (32% w/w. 8.0 ml) at room temperature for about 1 hour with stirring. Diethyl ether (50 ml) is then added and the mixture set aside for three hours at 0° C. The solid precipitate is collected, washed with diethyl ether, and dried to give the desired product, 2-(glycylimino)-3-methyl-1,3,4-thiadiazoline-5-sulphonamide hydrobromide, m.p. 209°–210° C. (0.4 gm).

EXAMPLE XXI

Preparation of
2-L-(Alanylimino)-3-Ethyl-1,3,4-Thiadiazoline-5-Sulphonamide Hydrobromide Observing once again the reaction and recovery procedures set out in Example XX and applied to the product of Example XVII (0.5 gm), the desired product, 2-L-(alanylimino)-3-ethyl-1,3,4-thiadiazoline-5-sulphonamide hydrobromide is obtained as pale cream colored crystals, m.p. 203°–205° C., 0.35 gm.

EXAMPLE XXII

Preparation of
2-L-(Phenylalanylimino)-3-Methyl-1,3,4-Thiadiazoline-5-Sulphonamide Hydrobromide Observing once again the reaction and recovery procedures set out in Example XIX and applied to the product of Example XVIII (0.5 gm), the desired product, 2-L-(phenylalanylimino)-3-methyl-1,3,4-thiadiazoline-5-sulphonamide hydrobromide is obtained as colorless crystals, m.p. 223°–224° C., 0.45 gm.

EXAMPLE XXIII

Preparation of
2-L-(Valylimino)-3-Methyl-1,3,4-Thiadiazoline-5-Sulphonamide Hydrochloride The product of Example XIX (0.5 gm) is dissolved in dry methanol (50 ml) containing concentrated hydrochloric acid (0.05 ml) and stirred with 10% palladium on charcoal (0.2 gm) under an atmosphere of hydrogen gas at about 15 p.s.i. for about 24 hours. The solution is filtered through "Celite" and evaporated under vacuum to give a solid which is crystallized from ethanol to give the desired product, 2-L-(valylimino)-3-methyl-1,3,4-thiadiazoline-5-sulphonamide (0.3 gm), m.p. 198°–199° C.

In general, the hydrobromide salts of the above products may be converted into the corresponding hydrochloride salts or salts of other acids by conventional methods, in particular the use of ion exchange resins, by operations familiar to those skilled in the art. Similar results have been obtained for the hydrochloride salts and for the hydrobromide salts.

Yet another way of preparing these protected 2-N-aminoacyl-3-alkyl-1,3,4-thiadiazoline-5-sulphonamides is from the condensation of a suitably N-protected amino acid with a 3-alkyl-2-imino-1,3,4-thiadiazoline-5-sulphonamide. A particularly desirable process for achieving this objective is one wherein the selected acid reactant in anhydrous pyridine is admixed with anhydrous tetrahydrofuran at reduced temperatures, on the order of $-15°$ C., and a condensation agent is added dropwise thereto with stirring, the agent being added in slight excess of the molar amount of reactant acid present while maintaining the temperature at reduced values. For preparation of compounds having the formula

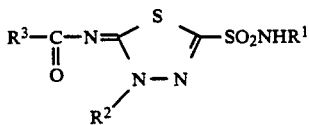

a solution of the selected sulphonamide in anhydrous tetrahydrofuran is then added slowly while maintaining the reaction medium at low temperatures. After a period of stirring under reduced temperatures on the order of about four hours, the reaction mixture is allowed to warm with stirring, and evaporated to a solid under reduced pressures. The solid is then partitioned in a water: lower alkyl ester wash, and the organic phase separated, washed, and dried over a suitable drying agent. The resulting anhydrous solution is then filtered and evaporated under reduced pressure to recover the sulphonamide product as a solid. The following specific, but not limiting, example serves to further illustrate this invention.

EXAMPLE XXIV

Preparation of
2-(N-Carbobenzyloxy-L-Alanylimino)-3-Methyl-1,3,4-Thiadiazoline-5-Sulphonamide Anhydrous pyridine (3.45 gm, 20mmole) and 2-(N-carbobenzyloxy)-L-alanine (5.1 gm 20 mmole) are stirred and admixed in a 250 ml round bottom flask with anhydrous tetrahydrofuran (40 ml) at $-15°$ C. To the stirred flask is added dropwise isobutyl chloroformate (3.0 gm, 22 mmole) and the contents of the flask stirred for an additional 5 minutes. A solution of 2-imino-3-methyl-1,3,4-thiadiazoline-5-sulphonamide (3.75 gm, 20 mmole), (R. W. Young, K. H. Wood, J. A. Eichler, J. R. Vaughan, and G. W. Anderson, J. Amer. Chem. Soc., 1956, 78, 4649–4654) in 200 ml dry tetrahydrofuran is then added slowly at $-15°$ C. while the stirring is continued.

After 3 hours the reaction mixture is allowed to warm to room temperature and the stirring is continued overnight. The mixture is then evaporated to dryness under reduced pressure and the solids partitioned between water and ethyl acetate (1:1, V/V, 400 ml). The resulting organic phase is washed with aqueous citric acid (200 ml 10% w/v), 100 ml water, 100 ml saturated brine, and dried over anhydrous magnesium sulphate.

After filtration, the solution is evaporated under reduced pressure and crystallized from ethanol to yield as product 4.0 gm 2-(N-carbobenzyloxy-L-alanylimino)-3-methyl-1,3,4-thiadiazoline-5-sulphonamide as a white solid having m.p. 106° C.

In the same way and using the same procedure with appropriate starting materials, the products of Examples XVI, XVII, XVIII and XIX were also prepared and found to be identical with the materials as prepared in these examples.

As previously stated, the compounds of the present invention find particular utility as carbonic anhydrase inhibitors. Acetazolamide, considered to be the most effective carbonic anhydrase inhibitor currently available, although some 330 times as active as p-aminobenzenesulfonamide, known also as a carbonic anhydrase inhibitor, suffers from the undesirable property of extremely low water solubility, on the order of about 0.01% w/v. The compounds of the present invention, either as free amines or as salts, are water soluble and, additionally, possess carbonic anhydrase inhibitory properties equal to and surpassing those of acetazolamide, as evidenced by the following tabular results.

| Compound | Molecular wt. | Conc. for 50% Inhibition |
|---|---|---|
| 2-(Glycylamino)-1,3,4-thiadiazole-5-sulfonamide hydrobromide | 318 | $1.0 \times 10^{-8}$ M |
| 2-(L-Alanylamino)-1,3,4-thiadiazole-5-sulfonamide hydrobromide | 342 | $3.0 \times 10^{-8}$ M |
| 2-(L-N-Carbobenzyloxyphenyl-thiadiazole-5-sulfonamide hydrobromide | 512 | $0.5 \times 10^{-8}$ M |
| 2-(L-phenylalanylamino)-1,3,4-thiadiazole-5-sulfonamide hydrobromide | 394 | $0.9 \times 10^{-8}$ M |
| 2-(Glycylimino)-3-methyl-1,3,4-thiadiazoline-5-sulphonamide hydrobromide | 332 | $0.9 \times 10^{-8}$ M |
| 2-(L-Alanylimino)-3-ethyl-1,3,4-thiadiazoline-5-sulphonamide hydrobromide | 370 | $1.1 \times 10^{-8}$ M |
| 2-(L-Phenylalanylimino)-3-methyl-1,3,4-thiadiazoline-5-sulphonamide hydrobromide | 406 | $0.7 \times 10^{-8}$ M |
| 2-(L-Valylimino)-3-methyl-1,3,4-thiadiazoline-5-sulphonamide hydrobromide | 384 | $1.0 \times 10^{-8}$ M |
| Acetazolamide | 222 | $1.08 \times 10^{-8}$ M |

For topical application, the selected compound is carried in an inert, non-tissue irritating and non-toxic diluent admixed with commonly known adjuvants. A number of such formulations are known in the art and commonly referred to, for example, in the Physician's Desk Reference for Ophthalmology (1982 Edition, published by Medical Economics, Inc., Ordell, N.J.) wherein a number of sterile ophthalmologic ocular solutions are set forth, for example, at pp. 112–114, the disclosure of which is hereby incorporated by reference.

The carbonic anhydrase inhibiting compounds of the present invention are present in amounts of from about 0.1 up to 5 percent by weight, based on the weight of the formulation and the solubility. Preferably, the compound is present in an amount of from about 0.5 to about 4 percent by weight and in tests conducted to date, highly effective compositions have utilized the active compounds at the 1 to 3 percent by weight level. Preferably the topical formulation is administered 1 to 5 times daily with a daily dosage of 0.1 mg to 20 mg.

In producing the treatment formulations, the selected sulfonamide, or a pharmaceutically acceptable salt thereof, may be admixed with suitable carriers, preservatives, bacteriostats, viscosity adjusting agents and the like as are commonly employed in the art. Carriers which may be used in conjunction with the active sulfonamides can be generally any of the pharmaceutically acceptable carriers which will yield a particular dosage form of desired consistency when admixed with the sulfonamide. Suitable carriers include water, water admixed with water-miscible solvents, PVP, polyalkylene glycols, cellulosic derivatives, gelatin, natural gums, and the like. It is clear that for the purposes of this invention, the particular carrier used is not critical.

While the diluents used are not part of the present invention, it is preferred that the diluent be selected from such well known diluents as water and polyvinyl alcohol. Most preferably, water is utilized as the diluent.

The compositions also advantageously contain small, but effective, amounts of a wetting agent and an anti-bacterial agent and have a pH in the range of from about 6.5 to about 7.8, preferably from about 6.8 to about 7.2.

Commonly used wetting agents suitable for use in the present formulations are such as those disclosed at pp. 112–114 of the Physician's Desk Reference for Ophthalmology, previously referred to. One such suitable wetting agent is Tween, particularly Tween 80. A particularly suitable wetting agent is polyoxyethylene 20 sorbitan mono-oleate (polysorbate). The selected wetting agent is included in the formulation in amounts of from about 0.02 to 5 percent by weight, preferably 0.02 to about 0.1 percent by weight, based on the total weight of the formulation.

Anti-bacterials are likewise known and commonly employed in such compositions. Suitable anti-bacterials include, for example, benzalkonium chloride, parabens, chlorobutanols, thimerosal and the like, and are generally included in the formulations in an amount of from about 0.004 to about 0.5 percent by weight, preferably from about 0.02 to 0.05 percent by weight, based upon the total weight of the composition.

Suitable viscosity adjusting agents include the cellulosic derivatives, such as alkyl celluloses, hydroxypropyl cellulose and the like, employed in amounts sufficient to produce the desired viscosity, generally from about 1 to about 10 mg./ml.

Additional agents commonly used in ophthalmic formulations may also be included, such as chelating agents, exemplified by disodium edetate.

The pH of the formulation is adjusted to the desired level by the use of such commonly known buffering agents as alkali metal and alkali earth metal carbonates, bicarbonates, borates, citrates and the like, present in amounts sufficient to produce the desired pH.

In producing the glaucoma treatment compositions, the various components are admixed in accordance with any of the methods well known in the pharmaceutical art, the order of mixing not being critical.

The compounds of the present invention are water-soluble, but also have a lipid solubility factor to allow transfer across the eye, and function effectively as carbonic anhydrase inhibitors. The water solubility imparts also an ease of preparation for the glaucoma treatment formulations.

Of the compounds falling within the generic formula

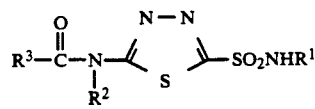

the most preferred compounds are 2-(glycylamino)-1,3,4-thiadiazole-5-sulfonamide, 2-(L-alanylamino)-1,3,4-thiadiazole-5-sulfonamide and 2-(L-phenylalanylamino)-1,3,4-thiadiazole-5-sulfonamide, as well their hydrochloride salts.

Of the compounds falling within the generic formula

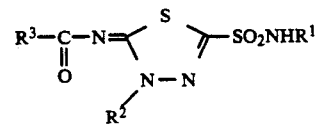

the most preferred compounds are 2-(glycylimino)-3-methyl-1,3,4-thiadiazoline-5-sulphonamide, 2-(L-alanylimino)-3-ethyl-1,3,4-thiadiazoline-5-sulphonamide, 2-(L-phenylalanylimino)-3-methyl-1,3,4-thiadiazoline-5-sulphonamide, and 2-(L-valylimino)-3-methyl-1,3,4-thiadiazoline-5-sulphonamide, as well as their enantiomers and hydrochloride salts.

For administration modes other than by eye drops, the sulfonamides may be utilized as the active ingredient in tablets, capsules, injectables and the like, with the particular dosage form produced in accordance with techniques generally known and accepted in the art. The dosage amounts in such formulations will vary, of course, depending upon such factors as age, general health and weight. Generally, such dosage units will contain the sulfonamide in amounts of from about 0.01 to 5 percent by weight, preferably from about 1 to about 3 percent by weight. Advantageously, in use, equal doses are administered 1 to 5 times daily, preferably 1 to 3 times daily, with the daily dosage regimen of the active sulfonamide being from about 125 mg up to 1500 mg, with the treatment continued for the duration of the condition treated. It is understood that the dosage amounts may be varied depending on such factors as patient tolerance and response.

The pharmaceutical carriers employed in conjunction with the active sulfonamide compounds may be liquid, semi-solid or solid. Exemplary of solid carriers are sugars, gums and cellulose. Semi-solid materials suitable for use as carriers are capsules and powders, while liquid carriers include water, alcohol, cellulose and PVA.

The following examples are offered to further illustrate the preparation of the novel glaucoma treatment compositions of this invention and the use thereof in controlling intraocular pressures.

In the following examples, ophthalmic formulations based on the sulfonamides appearing in Table I were tested at the Department of Ophthalmology laboratory of Albany Medical College, Albany, N.Y. using the rabbit eye model of New Zealand rabbits of both sexes weighing between 1.1 to 2.5 Kg. The IOP (intraocular pressure) was measured with an Alcon Application Pneumatonograph adapted for rabbit eyes, normal IOP in rabbits eyes generally being from 16 to 24 mm Hg.

All solutions tested were formulated in an aqueous vehicle and included the active sulfonamide, boric acid, potassium chloride, anhydrous sodium carbonate, benzalkonium chloride and EDTA, a pH of about 6.7, an osmolality of 290 mOsm, to result in a 2 percent w/v solution.

Drops of the aqueous solutions were applied to the eyes of the rabbits having normal IOP and the IOP thereof measured as a function of time. The eyes were continuously observed for onset of any adverse reaction, the pupil was periodically tested for light reactivity and the general reaction of the rabbits recorded. With each of the compounds tested, no adverse reaction was noted, either during the testing or during a follow-up period, with all eyes remaining clear and with the pupils light reactive.

In each testing, a single drop of the selected formulation was administered, the IOP monitored for four hours, and a second drop administered.

An example of a therapeutically useful composition containing the active sulfonamide in a 3 percent w/v solution with an osmolality of 290 mOsm would be prepared as follows.

| | |
|---|---|
| sulfonamide [2-(glycylamino)-1,3,4-thiadiazole-5-sulfonamide hydrochloride] | 30.0 mg/ml |
| boric acid, N.F. | 12.4 mg/ml |
| potassium chloride, USP | 7.4 mg/ml |
| sodium citrate, USP | 0.7 mg/ml |
| benzalkonium chloride (50% solution) and EDTA (0.5 mg/ml) | 0.04 mg/ml |
| water | Q.S. to 1 ml |

The pH is adjusted to about 6.7 with sodium hydroxide/hydrochloric acid.

Another useful formulation example is as follows.

| | |
|---|---|
| sulfonamide [2-(glycylamino)-1,3,4-thiadiazole-5-sulfonamide hydrochloride] | 30.0 mg/ml |
| polyethylene glycol 4000, USP | 10.0 mg/ml |
| povidone, USP | 16.7 mg/ml |
| pluronic F68 | 0.2 mg/ml |
| polyacrylamide | 5.0 mg/ml |
| hydroxyethylcellulose 52,000 (cellosize Q.P 5200) | 4.3 mg/ml |
| EDTA (dihydrate), USP | 1.0 mg/ml |
| boric acid N.F. | 10.0 mg/ml |
| sodium borate, USP | 1.5 mg/ml |
| benzalkonium chloride, USP 17% solution (Zephirin) | 0.236 ml |
| purified water | to 1 ml |

The pH is adjusted to about 6.7 with sodium hydroxide/hydrochloric acid.

We claim:

1. A compound of the formula:

$$R^3-\underset{\underset{O}{\|}}{C}-N=\!\!\!\!\underset{\underset{R^2}{\diagdown N-N}}{\overset{S}{\diagup}}\!\!\!\!-SO_2NHR^1$$

or a pharmaceutically acceptable salt thereof, wherein
$R^1$ is selected from the group consisting of H, —OH, —CN and —OCH$_3$;
$R^2$ is a methyl or a lower alkyl having from two to five carbon atoms;
$R^3$ is selected from the group consisting of HNHCHR$^4$—, R$^5$NHCHR$^4$—, R$^5$NHCH$_2$CHR$^4$—,

[pyrrolidine structures with H and R$^5$ substituents]

$R^4$ is a lower alkyl having two or five carbon atoms, or a naturally occurring amino acid side chain;
$R^5$ is selected from the group consisting of CH$_3$—, HCO—, CH$_3$CO—, and X—CH$_2$CO— wherein X is a halogen atom; and
stereoisomers thereof.

2. A compound according to claim 1, which is 2-(glycylimino)-3-methyl-1,3,4-thiadiazoline-5-sulphonamide or a pharmaceutically acceptable salt thereof.

3. A compound according to claim 1, which is 2-(L-alanylimino)-3-ethyl-1,3,4-thiaiazoline-5-sulphonamide or its enantiomer or a pharmaceutically acceptable salt thereof.

4. A compound according to claim 1, which is 2-(L-phenylalanylimino)-3-methyl-1,3,4-thiadiazoline-5-sulphonamide or its enantiomer or a pharmaceutically acceptable salt thereof.

5. A compound according to claim 1 which is 2-(L-valylimino)-3-methyl-1,3,4-thiadiazoline-5-sulphonamide or its enantiomer or a pharmaceutically acceptable salt thereof.

6. A compound according to claim 1, in the form of a salt produced by reaction with hydrobromic acid.

7. A compound according to claim 1, in the form of a salt produced by reaction with hydrochloric acid.

8. A compound according to claim 1, in the form of a salt produced by reaction with citric acid.

9. Method of treating glaucoma in a mammal, comprising administering to the mammal an effective amount of an active water-soluble carbonic anhydrase inhibitor having the formula:

$$R^3-\underset{\underset{O}{\|}}{C}-N=\!\!\!\!\underset{\underset{R^2}{\diagdown N-N}}{\overset{S}{\diagup}}\!\!\!\!-SO_2NHR^1$$

or a pharmaceutically acceptable salt thereof, wherein
$R^1$ is selected from the group consisting of H, —OH, —CN and —OCH$_3$;
$R^2$ is methyl or a lower alkyl having from two to about 5 carbon atoms;
$R^3$ is selected from the group consisting of HNHCHR$^4$—, R$^5$NHCHR$^4$—, R$^5$NHCHR$^4$—,

[pyrrolidine structures with H and R$^5$ substituents]

$R^4$ is selected from lower alkyl having two or five carbon atoms, or a naturally occurring amino acid side-chain; and $R^5$ is selected from the group consisting of $CH_3-$, $HCO-$, $CH_3CO-$ and $X-CH_2CO-$ wherein X is a halogen atom; and stereoisomers thereof.

10. The method of claim 9, wherein said inhibitor is administered topically.

11. The method of claim 9, wherein said inhibitor is administered systemically.

12. The method of claim 10, wherein said inhibitor is administered in the form of a pharmaceutically acceptable ophthalmic formulation.

13. The method of claim 12, wherein said formulation contains 0.01-5% by weight active inhibitor.

14. The method of claim 13, wherein said formulation contains 1-3% by weight active inhibitor.

15. The method of claim 12, wherein said formulation is administered 1-5 times daily.

16. The method of claim 15, wherein said formulation is administered such that the daily dosage is from 0.1-20 mg.

17. The method of claim 11, wherein said inhibitor is administered in the form of a pharmaceutically acceptable systemic formulation.

18. The method of claim 17, wherein said formulation contains 0.01-5% by weight active inhibitor.

19. The method of claim 18, wherein said formulation contains 1-3% by weight active inhibitor.

20. The method of claim 17, wherein said formulation is administered 1-3 times daily.

21. The method of claim 20, wherein said formulation is administered such that the daily dosage of the inhibitor is from 125-1500 mg.

22. The method of claim 9, wherein said inhibitor is 2-(glycylimino)-3-methyl-1,3,4-thiadiazoline-5-sulphonamide or a pharmaceutically acceptable salt thereof.

23. The method of claim 9, wherein said inhibitor is 2-(L-alanylimino)-3-ethyl-1,3,4-thiadiazoline-5-sulphonamide or its enantiomer or a pharmaceutically acceptable salt thereof.

24. The method of claim 9, wherein said inhibitor is 2-(L-phenylalanylimino)-3-methyl-1,3,4-thiadiazoline-5-sulphonamide or its enantiomer or a pharmaceutically acceptable salt thereof.

25. The method of claim 9, wherein said inhibitor is 2-(L-valylimino)-3-methyl-1,3,4-thiadiazoline-5-sulphonamide or its enantiomer or a pharmaceutically acceptable salt thereof.

26. The method of claim 9, wherein said inhibitor is administered topically in order to act as a prodrug through release of an aminoarylsulfonamide or a 2-amino-1,3,4-thiodiazole-5-sulfonamide as a result of enzymatic hydrolysis by aminopeptidase.

27. A pharmaceutically acceptable formulation useful in the treatment of glaucoma, comprising an effective amount of an active, water-soluble carbonic anhydrase inhibitor having the formula:

$$R^3-\underset{\underset{O}{\|}}{C}-N=\underset{\underset{R^2}{N-N}}{\overset{S}{\diagup}}-SO_2NHR^1$$

or a pharmaceutically acceptable salt thereof, wherein $R^1$ is selected from the group consisting of H, $-OH$, $-CN$ and $-OCH_3$;

$R^2$ is a methyl or a lower alkyl having from two to five carbon atoms;

$R^3$ is selected from the group consisting of $HNHCHR^4-$, $R^5NHCHR^4-$, $R^5NHCH_2R^5NHCH_2CHR^4-$, and the two pyrrolidine structures (with NH and NR⁵ respectively)

$R^4$ is a lower alkyl having two or five carbon atoms, or a naturally occurring amino acid side chain;

$R^5$ is selected from the group consisting of $CH_3-$, $HCO-$, $CH_3CO-$, and $X-CH_2CO-$ wherein X is a halogen atom; and stereoisomers thereof.

28. The formulation of claim 27, wherein the inhibitor is present in an amount of 0.01-5% by weight.

29. The formulation of claim 28, wherein the inhibitor is present in an amount of 1-3% by weight.

30. The formulation of claim 27, wherein said inhibitor is 2-(L-alanylimino)-3-ethyl-1,3,4-thiadiazoline-5-sulphonamide or its enantiomer or a pharmaceutically acceptable salt thereof.

31. The formulation of claim 27, wherein said inhibitor is 2-(L-phenylalanylimino)-3-methyl-1,3,4-thiadiazoline-5-sulphonamide or its enantiomer or a pharmaceutically acceptable salt thereof.

32. A compound of claim 1, wherein $R^3$ is $HNHCHR^4-$ and $R^4$ is a naturally occurring amino acid side chain, or a pharmaceutically acceptable salt thereof.

33. A compound of claim 32, wherein $R^4$ is a side chain of L-phenylalanine, or a pharmaceutically acceptable salt thereof.

* * * * *